United States Patent [19]

Strausser

[11] 4,444,757

[45] Apr. 24, 1984

[54] USE OF THYMOSIN AS AN ANTI-DIABETES AND ANTI-HYPERTENSIVE DISEASE AGENT

[75] Inventor: Helen R. Strausser, Roseland, N.J.

[73] Assignee: Research Corporation, New York, N.Y.

[21] Appl. No.: 321,783

[22] Filed: Nov. 16, 1981

[51] Int. Cl.³ .............................................. A61K 37/00
[52] U.S. Cl. ................................................ 424/177
[58] Field of Search ................................. 424/177, 95

[56] References Cited

U.S. PATENT DOCUMENTS 4,079,127  3/1978  Goldstein et al. ................... 424/177

OTHER PUBLICATIONS

Marchalonis–Cancer Biology Reviews, vol. 1 (1980) pp. 79, 80, 84–87, 91–95.

Marshall et al.–Recent Results in Cancer Research, vol. 75 (1980) pp. 100–105.
Marshall et al.–Chem. Abst. vol. 94 (1980) p. 77089j.
Yu et al.–Chem. Abst. vol. 94 (1980) p. 28635a.
Trivers–Chem. Abst. vol. 93 (1980) pp. 68 273s.

*Primary Examiner*—Sam Rosen
*Attorney, Agent, or Firm*—Scully, Scott, Murphy & Presser

[57] ABSTRACT

Methods are provided for the use of Thymus gland extracts, such as Thymosin, fraction 5, as an anti-autoimmune disease agent, useful in treating autoimmune diseases such as hypertension, lupus and diabetes. Thymosin, fraction 5, administration stimulated the development of a specific subclass of Thymus derived cells called Thymus suppressor cells which reduced the autoimmune state, thereby reducing hypertension, lupus, diabetes, and other autoimmune diseases.

3 Claims, 1 Drawing Figure

USE OF THYMOSIN AS AN ANTI-DIABETES AND ANTI-HYPERTENSIVE DISEASE AGENT

BACKGROUND OF THE INVENTION

1. Field of the Invention

This invention relates to a new method for treating autoimmune diseases such as hypertension, diabetes and lupus. Treatment requires the administration of a Thymus gland extract, designated Thymosin.

2. Description of the Prior Art

The importance of the thymus gland in the development and senesince of immunological competence in mammals is now generally accepted. Although the exact mechanism by which the thymus gland exerts control over the immune system is not known, it appears that a substantial portion of this control occurs via a hormonal mechanism. The thymus produces a family of polypeptides termed thymosin and perhaps several other thymic hormones and/or factors which play an important role in the maturation, differentiation and function of T-cells (Thymus-derived cells) and the immune response.

Thymosin, fraction 5, which has been widely employed in the biological investigations of thymosin, has been shown to contain 10–15 major components and 20 or more minor components, with molecular weights ranging from 1,000 to 15,000, as determined by analytical polyacrylamide gel electrophoresis and isoelectric focusing. Thymosin purification, characterization, and use is described in greater detail by Goldstein et al in U.S. Pat. Nos. 4,010,148 and 4,079,127 herein incorporated by reference. These patents describe the purification and use of Thymosin, and one of its components, Thymosin α.

Thymosin, fraction 5, refers to the fifth step in purification, that is, the product following the ultrafiltration and gel filtration (sephadex G-25) desalting of an ammonium sulfate precipitate from a thymus gland extract as shown below.

| Steps in Thymosin Purification | |
|---|---|
| Fraction 1 | 14,000 × g Centrifugation Product |
| Fraction 2 | 80° C. Heat step filtrate |
| Fraction 3 | Acetone Precipitate |
| Fraction 4 | Ammonium sulfate precipitate |
| Fraction 5 | Ultrafiltration & Sephadex G25 desalted peak |

Thymosin, fraction 5, and Thymosin α, have been used to reconstitute immune functions in mammals lacking some Thymosin-dependent function which causes an immune disease such as Thymus hypoplasia and abnormal immunoglobulin synthesis. Thymosin, fraction 5, has also been used in combination with cancer chemotherapy and radiotherapy to prolong survival time. (Journal of the American Medical Association, July 17, 1981, Vol. 246, No. 3, page 205). Apparently Thymosin, fraction 5, contains those hormones necessary for the proper development of particular subsets of T-lymphocytes. Thymosin α, has been shown to circulate at high levels in newborn children but to decline with age. The other hormonal elements present in Thymosin, fraction 5, have not been purified or well characterized. Thus the properties of Thymosin, fraction 5, may be due to a combination of one or more of the hormone-like polypeptides present. However, the prior disclosures of the use of thymus extracts such as Thymosin, fraction 5, did not disclose the treatment of autoimmune diseases.

An autoimmune disease involves an animal's immune system harmfully attacking the tissues of its own body. Therefore, a fraction active in stimulating the immune response, such as Thymosin, might be anticipated to aggravate and increase the pathology in an autoimmune disease. Surprisingly, Thymosin, fraction 5 acts to decrease autoimmunity. This unexpected result could only be discovered through the use of a particular animal disease model system such as the spontaneous hypertensive rat (SHR) system. In a normal animal, Thymosin, fraction 5, would not have any observable effect on hypertension because the animal would have normal blood pressure. Thus, the use of a model such as the SHR system was necessary to detect the anti-autoimmune affects of Thymosin, fraction 5. Previously, it was not recognized that hypertension, diabetes and other disease states had an autoimmune component as their cause. Therefore, an unrecognized need for Thymosin treatment existed and recognition of this need and the effectiveness of Thymosin treatment of autoimmune diseases are the central concepts of this invention.

SUMMARY OF THE INVENTION

It is the object of this invention to provide a novel method for treating autoimmune diseases such as hypertension in mammals.

A further object is to provide a method for treating hypertension in mammals by administration of Thymus extracts such as Thymosin, fraction 5.

A further object is to provide a method for treating hypertension in mammals by administration of Thymosin fraction 5, to induce the growth of a T-suppressor cell population and thus reduce the autoimmune state, thereby reducing the blood pressure and clearing the circulatory system of immune complexes.

Further objects of the invention will become apparent from the disclosure which follows.

These objects have been attained by a process for treating autoimmune diseases, such as hypertension in mammals, comprising administering to a mammal a therapeutically effective amount of Thymosin, fraction 5.

DETAILED DESCRIPTION OF THE PREFERRED EMBODIMENTS

Figure 1:
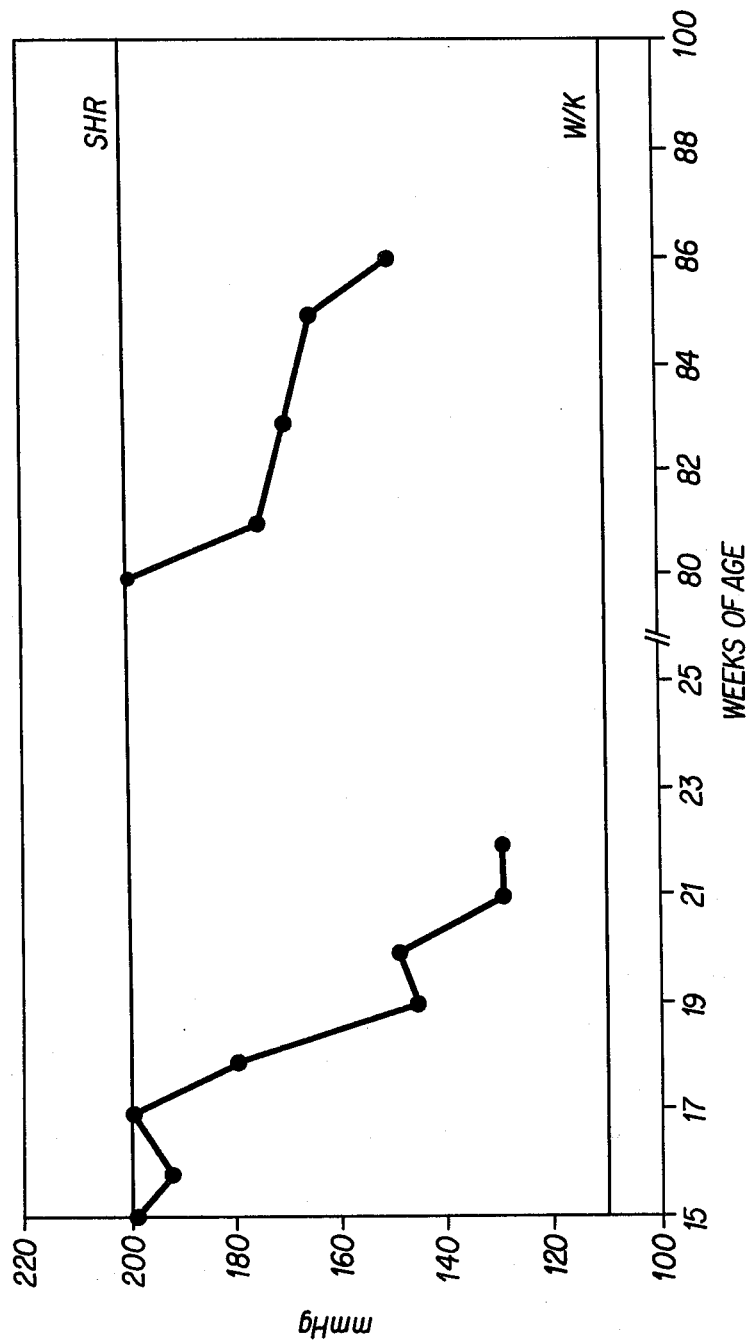
FIG. 1 is a graphic illustration of the blood pressure measured by a tail cuff of untreated control W/K and spontaneous hypertensive rats (SHR) and Thymosin, fraction 5, treated W/K and SHR at various weeks of age. Each data point represents the average blood pressure of animals in that part of the study.

Previously, it was not known that thymus extracts, such as Thymosin, fraction 5, could be used to treat autoimmune diseases. Also, it was not known that some types of hypertension, and diabetes were autoimmune diseases. Therefore, it is a new, unanticipated use for thymus extracts such as Thymosin, fraction 5, to be used to treat autoimmune diseases. The dosage of Thymosin, fraction 5, required to treat autoimmune diseases may vary depending upon the type of disease and the severity of the disease state. Thymosin, fraction 5, can be conveniently produced by the following procedures.

Thymus tissue derived from a suitable mammalian source, such as bovine, calf, human, rat, mouse or other similar source was quick frozen when fresh and stored for later use. As needed, Thymus tissue was thawed and trimmed free of adipose tissue. Generally it is desirable to use up to 5 Kg of tissue per batch and this description will relate to a standard 5 Kg batch. For larger batches of Thymus tissue increase all measurements proportionally. It is important to take normal precautions against microbiological contamination and the fractions should be routinely checked for pyroginicity by both the limulus endotoxin assay (Cooper et al, J. Lab. Clin. Med. 78, 137-138 (1973) and the rabbit pyrogenicity assay (McClosky et al., (1971)). Pyrogen free sterile water was used, throughout all procedures herein described and they were performed at 4° C. unless otherwise stated.

Fraction 1 resulted from the following procedures. Thymus tissue was homogenized in three volumes of dilute aqueous saline solution such as 0.15 M NaCl containing an anti-foaming agent such as 1% octyl alcohol (V/V) in a suitable blender for from 2 to 3 minutes, preferably 3 minutes at top speed. The resulting homogenate was then centrifuged at from 12,000 to 14,000 xg., preferably at about 14,000 xg. to sediment the nuclear material leaving a yellow supernatant. This supernatant was fraction 1.

Fraction 2 resulted from the following procedures. Two liter portions of the supernatant are heated with stirring to 80° C. in a boiling water bath. The voluminous precipitate of heat-denatured protein was removed by filtration. This clear yellow filtrate solution was fraction 2.

Fraction 3 resulted from the following procedures. After cooling to 4° C., the clear yellow filtrate was added slowly, with stirring, to 5 volumes of acetone at a temperature of $-20°$ to $-5°$ C., preferably at about -10° C. The precipitate was collected on a large Buchner funnel, washed with several volumes of cold ($-10°$ C.) acetone, and dried in a dessicator under reduced pressure leaving only a white powder. This white powder was fraction 3.

Fraction 4 resulted from the following procedures. Fraction 3 was suspended in about 10 volumes of 10 mM NaPO$_4$, pH 7.0 and stirred at 25° C. for 30 to 90 minutes, preferably 60 minutes. A small amount of insoluble residue was removed by centrifugation at from 12,000 to 15,000 xg., preferably at about 15,000 xg. and the sample protein concentration was adjusted to about 25 mg/ml. as determined by the Lowry procedure (Lowry et al, J. Biol. Chem. 193, 265-275 (1951)). Saturated ammonium sulfate solution (approximately 4.1 Molar) was adjusted to pH 7.0 with ammonium hydroxide and slowly added to the thymus extract (33.3 ml to each 100 ml of solution). This solution was stirred for 5 to 60 minutes, preferably 60 minutes and the resulting precipitate was collected by centrifugation at from 5,000 to 15,000 xg., referably 15,000 xg. This precipitate was fraction 4.

Fraction 5 resulted from the following procedures. The precipitate (fraction 4) was dissolved in about 10 nM of Tris Hcl, pH 8.0 at a concentration of from 8 to 12 mg/ml protein, preferably 10 mg/ml protein. This solution was subjected to ultrafiltration at room temperature in a hollow fiber system, preferably an Amicon DC-2-system-concentration mode, HIDPIO membrane cartridge. Such ultrafiltration serves to remove materials having a molecular weight of 15,000 d. or greater.

The filtrate from the ultrafiltration was collected at 4° C., concentrated by rotary evaporation under reduced pressure and desalted on a 5×80 cm gel filtration column (Sephadex G-25 fine) equilibrated with dionized water. The protein peak which eluted in advance of the salt and nucleotide peak was pooled, concentrated by rotary evaporation, and dried by lyophilization. This material was fraction 5. Fraction 5 was stored and dissolved as needed.

Further steps in purification to further isolate the anti-autoimmune fractions can be made. Such steps consist of ion exchange chromatography, gel filtration centrifugation, polyacrylamide gel electrophoresis, and affinity chromatography. In each step those fractions exhibiting anti-autoimmune activity are pooled and concentrated. The genes coding for the anti-autoimmune peptides in Thymosin, fraction 5, can be inserted into microorganisms using restriction endonucleases and plasmid vectors according to the method of Cohen et al U.S. Pat. No. 4,237,224. Such microorganisms can then be used to produce anti-autoimmune Thymosin fractions, which can be purified and used for treatment of autoimmune disease.

The following specific Examples 1–5 are a comparison of two genetic strains of rats. The first strain is a spontaneously hypertensive rat (SHR) which contains both a group of old rats and a group of young rats. A strain of rat designated Wistar/Kyoto (W/K) were used as a control group. Both the spontaneously hypertensive rats and the Wistar/Kyoto controls were compared using one group of animals 15 weeks old and one group of animals 80 weeks old. Thymosin, fraction 5, was administered subcutaneously to the SHR and lowered the blood pressures within 4 weeks of the start of treatment. Also examined in the experimental animals was the T-cell rosette formation with guinea pig erythrocytes and the lymph node T-cell response to the mitogenes concanavalin A (Con A) and phytohemagglutinin (PHA). Thymosin, fraction 5, over a period of 7 weeks also increased the size of the Thymosin gland in the older hypertensive animals, while no similar effect was observed in the W/K controls. Thymosin, fraction 5, also lowered the high level of prostaglandin E to normal while decreasing the immune complex deposition in the kidney. The ability of Thymosin, fraction 5, to reduce spontaneous hypertension in rats, resembles the supression of an autoimmune disease due to a depression in thymus cell activity.

The following examples are based upon a genetic strain of spontaneous hypertensive rats (SHR) developed by Okamoto Aoki in 1963 (JAP. CIR. J. 27, 282-293). This animal model was used in the following examples to study idiopathic essential hypertension. Human hypertension has also been found to have a genetic basis with a high incidence in patients having the cell surface glycoproteins collectively designated the human lukocyte antigens (HLA) in group B8. The SHR model develops high blood pressure of about 200 ml Hg by 12 weeks of age and they inherit a pattern of cardiovascular difficulties which also appear at about the same age and become worse with time. The Thymus of the hypertensive rats develop severe hypertensive vascular disease after 1 year of age and have marked hyperplasia and hypertrophy of the epithelial tissue. These ultrastructure features suggest the involvement of an autoimmune mechanism. The following examples demonstrate a novel method for treating both young and old spontaneous hypotensive rats with Thymosin, fraction 5. This treatment was evaluated by monitoring mitogen reactivity, rosette formation, prostaglandin E levels, immune complex deposition and blood pressure effects on both young and old hypertensive rats and control W/K rats.

EXAMPLE 1

Decrease In Blood Pressure Following Thymosin treatment

The blood pressure of all Thymosin treated spontaneous hypertensive rats begins to fall about 2 weeks after the start of treatment with Thymosin, fraction 5. This is illustrated in FIG. 1 which summarizes the results of studies performed on 40 spontaneous hypertensive rats and 20 Wistar/Kyoto rats which had not been part of any prior experimental procedures. The treatment was begun at the ages shown in Table 1. There were two groups of animals, one 15 weeks of age and one 80 weeks of age. Following the start of the experimental procedure, body weights and blood pressure measurements were made weekly and at the termination of the treatment.

TABLE 1

The number of animals in each group at the start of the experiment and used in both blood pressure and all immunological studies.

| Strain | Treatment | Age (weeks) 15 | 80 |
|---|---|---|---|
| SHR | none | 8 | 16 |
| SHR | thymosin | 8 | 8 |
| W/K | none | 6 | 6 |
| W/K | thymosin | 6 | 6 |

The Thymosin, fraction 5, used in these studies was from Hoffman LaRoche lot No. c-100836 and was reconstituted in sterile saline, filtered through a Milex filter from Millipore, Bedford, Me.); and administered subcutaneously to the 15-week old W/K and SHR three times weekly for six weeks at a dosage of 1 mg/kg body weight (adjusted weekly). The 80-week old animals were given injections of Thymosin, fraction 5, three times weekly, (1 mg/kg per body weight, adjusted weekly) for 4 weeks followed by daily injections at the same dose for 2 weeks prior to sacrifice. The Thymosin preparation used in these experiments was free of endotoxin contaminants.

TABLE 2

Blood pressure (x ± SD) of untreated and treated male and female SHR from 15-22 weeks of age. Four of the untreated from each of these groups as well as all thymosin treated animals were used for immune system evaluations.

| | Male SHR | | Female SHR | |
|---|---|---|---|---|
| Week | (n = 10) untreated | (n = 4) treated | (n = 10) untreated | (n = 4) treated |
| 15 | 213 ± 15 | | 175 ± 13 | |
| 16 | 215 ± 15 | 193 ± 5 | 183 ± 12 | 166 ± 10 |
| 17 | 207 ± 20 | 200 ± 0 | 185 ± 10 | 192 ± 5 |
| 18 | 220 ± 14 | 179 ± 16 | 171 ± 6 | 191 ± 10 |
| 19 | 206 ± 5 | 146 ± 16 | 190 ± 14 | 142 ± 3 |
| 20 | 204 ± 9 | 150 ± 9 | 182 ± 15 | 130 ± 7 |
| 21 | 210 ± 10 | 132 ± 4 | 186 ± 11 | 132 ± 2 |
| 22 | 190 ± 10 | 132 ± 2 | 176 ± 10 | 104 ± 5 |

At the end of the experiment the spleen and lymph nodes were removed aseptically into sterile petri dishes containing 5 ml complete RPMI 1640 medium with 25 mM Hepes buffer, 200 mM glutamine, 10% heat inactivated fetal bovine serum (Microbiological Associates, Walkersville, MD), 0.1% gentamycin (Schering Laboratories, Kenilworth, N.J.) or 1% penicillin-streptomycin solution containing 10,000 microgram per ml streptomycin and 10,000 units per ml penicilin (GIBCO, Grand Island, NY). The Thymus glands were placed in a petri dish containing 5 ml Hanks Balanced Salt Solution (HBSS, Gibco). Spleen and lymphocyte cell suspensions were also prepared.

In FIG. 1 the measurement of blood pressure was made through indirect tail cuff measurements of both the control and Thymosin treated animals. Each data point represents the average blood pressure of animals in that part of the study. The 15 week old SHR received 1 mg/kg 3 times weekly during the period indicated by the bar. The 80 week old SHR group received 1 mg/kg 3 times weekly followed by 1 mg/kg/day beginning at week 84. As can be seen in FIG. 1, the blood pressure of the 15 week old SHR dropped a total of 70 mm Hg over the 7 week treatment period, while the 80 week old SHR fell 50 mm Hg and more rapidly as the treatment schedule was increased from 3 times per week to daily injections. The control animals, both 15 and 80 week old W/K did not change their blood pressure after Thymosin, fraction 5, treatment. The total weight of both the SHR and the W/K animals were unchanged by this treatment as compared to untreated control animals. This reduction in blood pressure due to administration of Thymosin, fraction 5, in both young and old SHR demonstrated the ability of Thymosin treatment to reduce hypertension. There was no change in the W/K control animals since they had no hypertension to correct.

EXAMPLE 2

Mitogenic Responses of Lymph Node Cells

Using the lymph node cells isolated in Example 1 from 20 week old male and female SHR and W/K, the mitogenic responses to concanavalin A showed no significant changes following Thymosin, fraction 5, treatment. Lymph node cells from 80 week old rats not stimulated by concanavalin A showed similar tritiated thymidine uptake, regardless of Thymosin treatment. This indicated similar DNA replication. The reactivity of the male and female W/K remained unchanged following Thymosin treatment. Unlike the 20 week old animals, the lymph node T-cell response to concanavalin A of the treated 80 week old female spontaneous hypertensive rats increased as much as 100-fold following Thymosin treatment as shown in the bottom of Table 3.

TABLE 3

Mitogenic responses of lymph node cells ($5 \times 10^6$ cells/ml) from 80 week old SHR and W/K (x ± SE).

| Strain | Sex | n | untreated | n | thymosin treated |
|---|---|---|---|---|---|
| W/K | M | 3 | 84,651 ± 4,491 | 3 | 66,917 ± 1,478 |
| SHR | M | 4 | 3,161 ± 526 | 4 | 10,852 ± 2,022 |
| W/K | F | 3 | 64,936 ± 1,479 | 3 | 61,158 ± 20,970 |
| SHR | F | 4 | 409 ± 57 | 4 | 47,799 ± 1,112 |

Concanavalin A is a plant lectin which binds specific lymphocyte surface receptors which lead to the formation of a patch or cap which is internalized into the cell. The net effect of this binding is a stimulation of metabolism, including an increase in DNA synthesis, mitosis and cell division. This is generally referred to as a mitogenic response. Phytohemagglutinin A (PHA) is another plant lectin like Con A, but which is mitogenic for T-cells but not mature B-cells (bone-marrow derived cells). Following Thymosin treatment both the 80 week old W/K and the SHR showed a 3-fold stimulation in response to PHA. This response is measured by the uptake of $^3$H thymidine which indicates DNA synthesis. To illustrate the response, the W/K not Thymosin treated incorporated 15,480±7,425 (cpm, n=3) while the Thymosin treated response was 45,036±10,727 (cpm, n=3) when treated with PHA. The incorporation of $^3$H thymidine by SHR not Thymosin treated was 10,964±2,491 (cpm, n=3) and for Thymosin treated SHR was 27,507±318 (cpm, n=3) when treated with PHA. The incorporation of $^3$H thymidine in the presence of lipopolysaccharide (LPS) was not influenced by Thymosin treatment in either experimental group. These mitogenic results indicate the T-cell responses of the young SHR were relatively unaffected by treatment with Thymosin, fraction 5. However, the T-cell mitogenic responses with both treated and untreated W/K were significantly higher than with the age matched SHR when examining both the spleen and the lymph node response. The fact that the B-cell responses were similar in both the SHR and the W/K and did not vary with Thymosin treatment would indicate that Thymosin, fraction 5, predominantly affected T-cells. Con A stimulation, following Thymosin, fraction 5, treatment, was considerably greater than the PHA in the older animals. This would appear to be the stimulation by Con A of a Thymosin-responsive population of cells. It is thought that Con A affects both the immature and mature T-cell populations whereas receptors for PHA are not found on the immature T-cell population. All spleen cell and lymphocyte suspensions and their mitogens were prepared as described in Bendich et al (Clinical Experimental Immunology, 43, 189–194, 1981).

EXAMPLE 3

Formation of Thymocyte Rosettes

Thymocyte rosettes are formed by the binding of guinea pig erythrocytes on the surface of the thymocyte with a rosette defined as having at least 3 blood cells bound. The guinea pig rosette technique of Elfenbein and Winkelstein (Cellular Immunology, 37, 188–198, 1978) was used to form the rosettes. An equivalent amount of 1% (v/v) guinea pig erythrocyte suspension in HBSS was added to a suspension of thymocytes containing 4×10$^6$ cells/ml in HBSS. Fetal bovine serum (not heat inactivated) was added to a final concentration of 10% v/v. The mixture was incubated for 30 minutes at 22° C., centrifuged for 5 minutes at 4° C. and incubated for 60 minutes at 4° C. The pellet was then aspirated and the nucleated cells were counted under the light microscope. Rosettes were expressed as the percentage of thymocytes having greater than 3 erythrocytes bound. At least 200 thymocytes were counted for each sample.

Thymocyte rosette formation with guinea pig erythrocyes was not changed by thymosin treatment of the young SHR, however the young W/K rosettes were decreased in number by thymosin treatment as shown at the top of Table 4. The thymuses of the old SHR were quite small and, therefore, the number of mononuclear cells was insufficient for this assay procedure. However, with thymosin treatment, the size of the old SHR thymuses increased from an average of 26 to 195 mg and thus contained sufficient mononuclear cells for the rosette assay procedure. Rosette formation with the thymocytes of these 80 week old SHR was approximately 40%, while rosettes with the old W/K thymocytes also increased from 16% to 30% following treatment with thymosin, fraction 5. To summarize the effect of Thymosin, fraction 5, on rosette formation; it was observed that with the young W/K animals, thymosin, fraction 5, caused a significant reduction in rosette formation while there was a slight increase in rosette formation with the young SHR animals. However, thymosin fraction 5, treatment of the old SHR animals resulted in a significant increase in rosette formation (bottom Table 4). This indicates that thymosin, fraction 5, decreased the T-cell population in the W/K animals when young, but increased the T-cell population in the old W/K animals. The old SHR animals responsed to thymosin, fraction 5, with a large increase in the T-cell population.

TABLE 4

| Percentage of rosetted thymocytes (x ± SE). | | | | |
|---|---|---|---|---|
| Strain | Age | Treatment | Male | Female |
| W/K | 20 | none | 30 ± 3 | 36 ± 3 |
| W/K | 20 | thymosin | 2 ± 1 | 14 ± 2 |
| SHR | 20 | none | 24 ± 2 | 28 ± 4 |
| SHR | 20 | thymosin | 26 ± 2 | 38 ± 7 |
| W/K | 80 | none | 18 ± 2 | 15 ± 4 |
| W/K | 80 | thymosin | 32 ± 8 | 29 ± 5 |
| SHR | 80 | none | insufficient cells | insufficient cells |
| SHR | 80 | thymosin | 42 ± 5 | 35 ± 5 |

EXAMPLE 4

Prostaglandin Production By Spleen Cells

Using the spleen cells isolated from the animals in Example 1, prostaglandin E (PgE) production was measured using 2 ml of each spleen cell suspension (5×10$^6$ cells/ml) incubated on flat bottom plates for 24 hours at 37°, in a humidified, 5% CO$_2$ enriched atmosphere. One ml of supernatant was added to a polypropylene tube and citrated. Prostaglandin E extraction and radioimmunoassay techniques were performed by the method of Poleschuck and Strausser (prostaglandins and Medicine, 4, 363–372, 1980).

As shown in Table 5, spleen cell production of prostaglandin E was markedly higher (45%) in the young SHR as compared to the young W/K. Treatment with thymosin, fraction 5, reduced the high PgE level in the SHR to that of the control W/K. One type of spleen cell, mononuclear phagocytes, has been shown to produce prostaglandin E when in contact with immune complexes. Therefore, a reduction in PgE could indicate a reduction in PgE producing mononuclear phagocytes, immune complexes or both. Prostaglandin E, is an immuno-suppressive agent and could be expected to inhibit the formation of antibody-antigen complexes since it may decrease antibody production. However, here the old SHR did not demonstrate an increase in prostaglandin E as compared to the young SHR. It is possible that the insufficient production of prostaglandins in the aged SHR resulted from the lack of or from the overloading of Fc receptors on macrophages when in contact with immune complexes. A similar defect may be present in lupus patients, (erthematosus, vulgaris etc.) where prostaglandin E is also produced in low amounts (Poleshuck et al, Prostaglandins and Medicine, 1981). It is suggested that thymosin, fraction 5, increases suppressor activity of lupus lymphoid cells thereby decreasing production of prostaglandin E. Therefore, by analogy spontaneous hypertension in rats may be similar to lupus in that both seem to be due to a deficiency of immune-suppressor activity of a subpopulation of T-suppressor cells, which may be designated thymosin-responsive lymphocytes.

TABLE 5

| Prostaglandin production by spleen cells ($5 \times 10^6$ cells). | | | |
|---|---|---|---|
| Strain | Age | Treatment | Pg/ml (x ± SD) |
| W/K | 20 | none | 300 ± 10 |
| W/K | 20 | thymosin | 259 ± 10 |
| SHR | 20 | none | 510 ± 30 |
| SHR | 20 | thymosin | 229 ± 10 |
| W/K | 80 | none | 229 ± 10 |
| W/K | 80 | thymosin | 317 ± 20 |
| SHR | 80 | none | 259 ± 10 |
| SHR | 80 | thymosin | 229 ± 10 |

Another parallel to the SHR is provided by the immune response in the diabetic mouse where depression of the immune response with anti-lymphocyte serum caused remission of diabetes. (Warchalowski and Strausser, Immunology Communications, 8, (4), 443-455, 1979). The use of anti-thymocyte serum in SHR animals decreased blood pressure to normal W/K levels (Bendich et al, Biochemical Biophysical Research Communications, 99, 600-607, 1981). Therefore, it is possible that the administration of thymosin increases suppressor cell activity and therefore both thymosin, fraction 5, and anti-thymocyte antibodies may cause a reduction of autoimmune reactions. Based upon this information it is suggested that thymosin, fraction 5, is a therapeutic agent which could result in the remission of human essential hypertension and other diseases, not yet classified as autoimmune.

Consistent with the autoimmune mechanism for the production of hypertension, it was noted that the kidney of the spontaneous hypertensive rat contained immune complex depositions while the thymosin treated SHR had a reduction in these immune complexes. Immune complexes have also been found in human hypertensive arteries and in the arteries of stressed rats. The immune complex deposits in the stressed rats were in the medial layer of the arteries, stained with peroxidase labeled anti-IgG and were determined to be immune complexes (Lattime and Strausser, Science, 198, 302-303, 1977). Therefore, at least one form of hypertension would appear to be produced by the formation of immune complexes and treatment with thymosin, fraction 5, decreases such complexes formation and therefore decreases hypertension. Similarly, other potential autoimmune diseases such as lupus and diabetes (multiple types of each) may also be treated with thymosin, fraction 5.

Other autoimmune diseases which are anticipated to be treatable in part with Thymosin are as follows:

(1) Hashimoto;s Thyroiditis (hypothyroidism)
(2) Thyrotoxicosis (hyperthroidism)
(3) Pernicious anemia
(4) Addison's disease (adreneal insufficiency)
(5) Pemphigus vulgaris
(6) Pemphigoid
(7) Sympathetic ophthalmia
(8) Goodpasture'syndrome
(9) Autoimmune hemolytic anemia
(10) Idiopathic Thrombocytopenic purpura
(11) Myasthenia gravis
(12) Allergic encephalitis
(13) Male infertility (sperm autoimmunity)
(14) Primary biliary cirrhosis
(15) Sjogren'disease
(16) Rheumatoid arthritis
(17) Systemic lupus erythematosus Thymosin exhibits both oral and parenteral activity and can be formulated in dosage forms for oral, minipump (osmotic), parenteral, or rectal administration. Solid dosage forms for oral administration include capsules, tablets and pills. In such solid dosage forms, the active compound is admixed with at least one inert diluent such as sucrose, lactose, or starch. In the case of capsules, tablets and pills, the dosage forms may be also comprise buffering agents. Tablets and pills can additionally be prepared with an enteric coating.

Liquid dosage forms for oral administration include syrups and elixirs containing inert diluents commonly used in the art, such as purified water. Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyl oleate.

Compositions for rectal administration are suppositories which may contain in addition to the active substance, excipients such as cocoa butter or a suppository wax.

A preferred method of administering Thymosin, fraction 5, in the method of this invention is to inject a composition comprising Thymosin and a slow release excipient, i.e., an excipient that is not immediately absorbed by the body wherein it slowly releases the Thymosin contained therein to provide a hightened serum concentration of Thymosin for an extended period of time.

Having now fully described the invention, it will be apparent to one of ordinary skill in the art that many changes and modifications may be made without departing from the spirit or the scope of the invention as set forth herein. Applicant does not wish to be bound by the theory that thymus supressor cells are the only process resulting in suppression of autoimmune diseases. Other processes or mechanisms not now known may also be stimulated by the administration of Thymosin which result in beneficial affects with autoimmune diseases.

What is claimed as new and desired to be secured by Letters Patent of the United States is:

1. A method of treating hypertension in a mammal in need of such treatment which comprises administering to said mammal an anti-hypertensive effective amount of thymosin.

2. A method of treating diabetes in a mammal in need of such treatment which comprises administering to said mammal an anti-diabetic effective amount of thymosin.

3. A method of claims 1 or 2 wherein the thymosin is Fraction 5.

* * * * *